United States Patent
Clark et al.

(10) Patent No.: US 8,829,467 B2
(45) Date of Patent: Sep. 9, 2014

(54) ANALYTICAL APPARATUS

(75) Inventors: Alastair Clark, Watford (GB); John Patrick Fitzgerald, Watford (GB); Stephen John Taylor, Amersham (GB); Robert Brian Turner, Chesham (GB)

(73) Assignee: Smiths Group PLC, London (GB)

( * ) Notice: Subject to any disclaimer, the term of this patent is extended or adjusted under 35 U.S.C. 154(b) by 890 days.

(21) Appl. No.: 11/883,069

(22) PCT Filed: Dec. 23, 2005

(86) PCT No.: PCT/GB2005/005053
§ 371 (c)(1),
(2), (4) Date: Jul. 26, 2007

(87) PCT Pub. No.: WO2006/079773
PCT Pub. Date: Aug. 3, 2006

(65) Prior Publication Data
US 2008/0142699 A1  Jun. 19, 2008

(30) Foreign Application Priority Data

Jan. 29, 2005  (GB) .................................. 0501940.1

(51) Int. Cl.
*H01J 27/00* (2006.01)
(52) U.S. Cl.
USPC .......... 250/423 R; 250/424; 250/281; 250/282
(58) Field of Classification Search
USPC ....... 250/423 R–423 F, 281–300, 316.1–326, 250/489
See application file for complete search history.

(56) References Cited

U.S. PATENT DOCUMENTS

| | | | | |
|---|---|---|---|---|
| 4,472,631 A * | 9/1984 | Enke et al. | ..................... | 250/281 |
| 4,963,738 A * | 10/1990 | Gundlach et al. | ............. | 250/326 |
| 5,304,797 A * | 4/1994 | Irie et al. | ........................ | 250/287 |
| 5,449,906 A * | 9/1995 | Osbourne | ...................... | 250/324 |
| 5,485,016 A * | 1/1996 | Irie et al. | ........................ | 250/288 |
| 5,684,300 A * | 11/1997 | Taylor et al. | ................... | 250/286 |
| 5,719,392 A * | 2/1998 | Franzen | ......................... | 250/282 |
| 6,121,608 A * | 9/2000 | Takada et al. | ................. | 250/288 |
| 6,225,623 B1 * | 5/2001 | Turner et al. | .................. | 250/286 |
| 6,252,225 B1 * | 6/2001 | Takada et al. | ................. | 250/288 |
| 6,300,626 B1 * | 10/2001 | Brock et al. | ................... | 250/287 |
| 6,437,327 B2 * | 8/2002 | Takada et al. | ................. | 250/288 |
| 6,521,887 B1 * | 2/2003 | Funsten et al. | ................ | 250/287 |
| 6,621,077 B1 * | 9/2003 | Guevremont et al. | ........ | 250/292 |
| 6,639,215 B2 * | 10/2003 | Takada et al. | ................. | 250/288 |
| 6,770,877 B2 * | 8/2004 | Ohta et al. | ..................... | 250/288 |

(Continued)

FOREIGN PATENT DOCUMENTS

| | | | | |
|---|---|---|---|---|
| WO | WO 93/11554 | 6/1993 | | |
| WO | WO 9311554 A1 * | 6/1993 | ............ | G01N 27/64 |
| WO | WO 2004/102178 A1 | 11/2004 | | |
| WO | WO 2004102178 A1 * | 11/2004 | ............ | G01N 27/64 |

*Primary Examiner* — Andrew Smyth
(74) *Attorney, Agent, or Firm* — Foley & Lardner LLP

(57) ABSTRACT

An IMS or other analytical instrument has a corona discharge needle (20) to ionize sample gases or vapours. A gate (3) is opened or closed to admit or prevent entry of the ions produced by the corona discharge to a drift chamber (4). The operation of the corona discharge needle (20) and the gate (3) are controlled such that the gate is open during at least two discharges, to admit faster ions produced by the most recent discharge together with slower ions produced by an earlier discharge.

22 Claims, 2 Drawing Sheets

(56) References Cited

U.S. PATENT DOCUMENTS

| | | | |
|---|---|---|---|
| 6,995,361 B2 * | 2/2006 | Kim et al. | 250/288 |
| 7,155,812 B1 * | 1/2007 | Peterson et al. | 29/610.1 |
| 7,265,346 B2 * | 9/2007 | Whitehouse et al. | 250/287 |
| 7,345,276 B2 * | 3/2008 | Wynn et al. | 250/287 |
| RE42,111 E * | 2/2011 | Park et al. | 250/396 R |
| 2001/0022344 A1 * | 9/2001 | Takada et al. | 250/288 |
| 2002/0074491 A1 * | 6/2002 | Fukuda | 250/288 |
| 2002/0125423 A1 * | 9/2002 | Ebeling et al. | 250/288 |
| 2002/0168778 A1 * | 11/2002 | Andrien et al. | 436/173 |
| 2003/0015657 A1 * | 1/2003 | Takada et al. | 250/288 |
| 2003/0155498 A1 * | 8/2003 | Kato | 250/281 |
| 2003/0213903 A1 * | 11/2003 | Ichimura et al. | 250/282 |
| 2004/0113067 A1 * | 6/2004 | Ohta et al. | 250/288 |
| 2004/0173739 A1 * | 9/2004 | Kim et al. | 250/288 |
| 2005/0199799 A1 * | 9/2005 | Takada et al. | 250/288 |

* cited by examiner

ANALYTICAL APPARATUS

This invention relates to analytical apparatus of the kind including an ionization source in an ionization region, a chamber, a gate at one end of the chamber adjacent the ionization region arranged to control passage of ions into the chamber, the ionization source including a corona discharge source and a control for controlling operation of the corona discharge source and the gate.

The invention is more particularly, but not exclusively concerned with ion mobility spectrometers (IMSs).

Ion mobility spectrometers (IMSs) are used to detect the presence of small quantities of airborne chemicals in vapours or gases at atmospheric pressure. An IMS has some means to ionize the sample chemicals, such as a corona discharge or a radioactive source. Where a corona discharge is used this may operate continuously or it may be pulsed. A gate admits the ions into one end of a drift chamber across which a voltage is applied to cause the ions to drift to the opposite end where they are collected on a collector plate. Where the corona discharge is pulsed, the gate is operated in synchronisation once every corona discharge event or group of discharge events. The time taken for an ion to pass from the gate to the collector plate is dependent on the mass, size, shape and charge on the ion. By measuring this time an indication can be provided of the nature of the chemical. The problems in handling radioactive sources has resulted in moves away from these to corona discharge ionisation sources, which may be either continuous or pulsed. A problem with pulsed ionisation sources arises because the period for which the gate is open only allows certain mobilities of ions to pass into the drift region. If the gate is held open for longer periods to admit a wider range of ion mobilities from the discharge, the resolution of the apparatus is substantially reduced.

It is an object of the present invention to provide alternative analytical apparatus.

According to one aspect of the present invention there is provided analytical apparatus of the above-specified kind, characterised in that the corona source is discharged at least twice for every time that the gate is opened and that the gate is arranged to pass faster ions produced by one discharge together with slower ions produced by a preceding discharge.

The apparatus is preferably arranged such that three corona discharges are produced during each period that the gate is open. The apparatus may be an ion mobility spectrometer and the chamber may be a drift chamber. The corona discharge source may include a corona needle extending within a metal tube. The gate preferably includes a first grid to which a pulsed voltage is applied. The apparatus may include a second grid adjacent the first grid to which a constant voltage is applied such as to draw ions through the gate. The switching period of the gate is preferably approximately 200 µs.

According to another aspect of the present invention there is provided a method of analyzing a sample gas or vapour comprising the steps of producing at least two corona discharges to ionize substances in the gas or vapour, alternately enabling and preventing admission of some of the ions produced by both discharges to a chamber, applying a field to the chamber to cause the admitted ions to move to a detector and providing an output from the detector.

An IMS spectrometer according to the present invention will now be described, by way of example, with reference to the accompanying drawings, in which.

Figure 1:
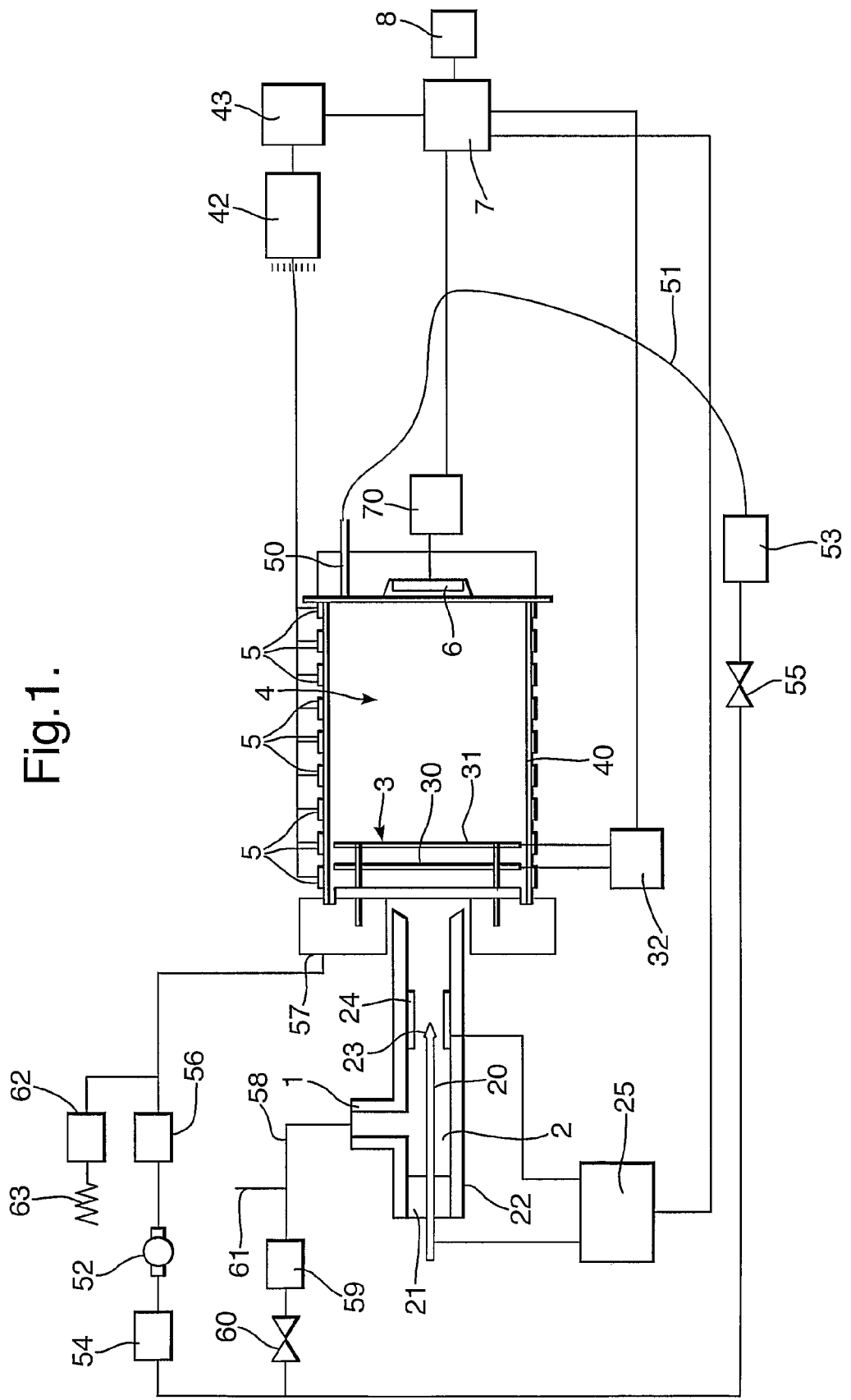
FIG. 1 shows the spectrometer schematically.

The spectrometer has an inlet 1 by which airborne chemicals and vapours enter the instrument and pass to an ionization chamber 2, where they are ionized. A gate 3 admits the ions to the left-hand end of a drift chamber 4 where they are caused to flow to the right-hand end by a voltage field applied to electrodes 5. Ions are collected on a collector plate 6 where they are detected to provide an output to a processing unit 7, which in turn provides an output representative of the nature of the chemical to a display 8 or other utilisation means.

The ionization chamber 2 has a metal corona needle 20 supported by an electrically-insulative ferrule 21 at one end to project co-axially along an electrically-insulative housing 22 and at right-angles to the inlet 1. The sharp point 23 of the needle 20 locates within a brass or nickel tube 24. A corona drive circuit 25 is connected between the needle 20 and the tube 24 to apply a high voltage of around 5 kV between them sufficient to produce a corona discharge effective to ionize chemicals and vapours admitted through the inlet 1. The right-hand end of the ionization chamber 2 opens into the left-hand end of the drift chamber 4 via the gate 3.

The gate 3 consists of two grid arrays 30 and 31 of fine electrical wires connected to a gating grid circuit 32. The gating grid circuit 32 applies a pulsed voltage to the first grid 30 and a constant voltage to the second grid 31. The second grid 31 helps define the field that draws the ions through the open gate. Operation of the gating grid circuit 32 is controlled by signals from the processing unit 7. The gate circuit 32 is able to float up to a few hundred volts with respect to the ionization source tube 24 in order to produce an accelerating potential that pulls ions from the corona point 23.

The drift chamber 4 takes the form of an electrically-insulative cylindrical tube or cell 40 having eight ring electrodes 5 extending coaxially around the outside of the tube and equally spaced from one another along the length of the tube. The electrodes 5 are connected to an electrode supply unit 42 that provides a field of about 0.24 kV/cm along the tube 40.

A gas inlet 50 opens into the right-hand end of the cell 40 by which a drift gas is admitted to the cell to flow from right to left against the direction of ion flow. The inlet 50 connects with piping 51 extending to the output of a pump 52 via two molecular sieves 53 and 54 and a valve 55. The inlet of the pump 52 connects via a third molecular sieve 56 to an exhaust outlet 57 at the left-hand end of the cell 40. The pneumatic circuit further includes a branch pipe 58 extending between the inlet 1 and the outlet of the pump 52 via a fourth molecular sieve 59 and a valve 60. The branch pipe 58 further includes an opening 61 between the sieve 59 and the inlet 1 by which external air for sampling is admitted to the spectrometer. Additional air can be admitted to the pneumatic system via a fifth molecular sieve 62 and a breather restriction 63. It can be seen that air flows along the cell 40 from the inlet 50 at its right-hand end to the exhaust outlet 57 at its left-hand end and that this exhausted air is filtered by the sieves 56, 54 and 53 before being re-circulated back to the inlet 50. The external air to be sampled is supplied to the spectrometer with a stream of filtered carrier air. The sieve 59 may include a chemical dopant selected to enhance identification of ion species of interest, as described in WO00/79261. The interior of the cell 40 is at substantially atmospheric pressure.

The collector plate 6 at the right-hand end of the cell 40 is connected with current amplifier 70, which in turn provides an output to the processing unit 7. The processing unit 7 produces a spectrum of the ions arriving at the collector plate 6 in the usual way. The spectrum need not take the form of a graphical representation but could be processed to provide a display of the name of the identified compound or an alarm when a specified compound was identified.

The pump 52 is energized to draw airborne molecules in through the opening 61 where they flow with carrier gas, which may include dopant, to the inlet 1 of the ionization chamber 2. The molecules are ionized by the discharge at the corona point 23 and, when the gate 3 is opened by the gating circuit 32, the ions pass into the left-hand end of the drift chamber 4. The field established in the cell 40 by the voltage on the electrodes 5 causes the ions to drift to the right along the cell against the flow of gas along the cell. The speed at which the ions move along the cell is determined by the size, shape and charge on the ions. When the ions reach the far end of the cell 40 they fall on the collector plate 6, thereby producing a small electrical charge on the plate, which is amplified by the amplifier 70 and supplied to the processing unit 7. The processing circuit 7 measures the time of flight of the ions, that is the time between opening the gate 3 and reception of a charge on the collector plate 6, and produces spectra against time with peaks representing different ions.

Figure 2:
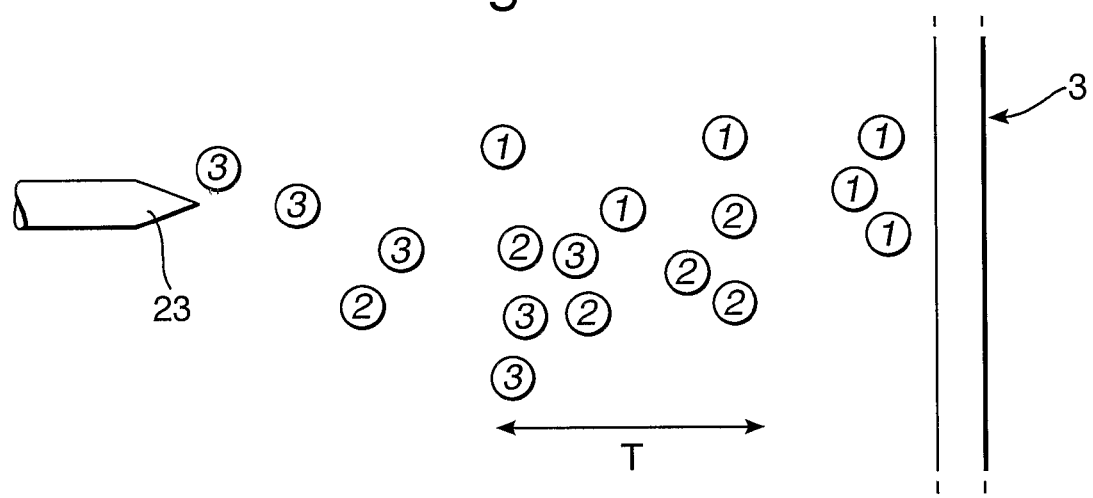
FIG. 2 illustrates ion production and gate switching.

The processing unit 7 also controls operation of the corona drive circuit 25. In particular, the corona discharge pulses produced are linked to the opening and closing of the gate 3. As can be seen in FIG. 2, at any one time the ionization region between the corona discharge 23 and the gate 3 will contain a mixture of slow and fast moving ions from different discharges. In FIG. 2, ions from three different discharges are illustrated, labelled "1", "2" and "3" respectively. The switching on and off of the corona discharge is sufficiently rapid that the slow-moving ions of one discharge will be close to or be overlapped by the fast-moving ions of the next, subsequent discharge. The gate 3 is opened for repeated periods of time T. The start of the open gate period is synchronised with the corona discharge such that it occurs when the slower ions of the first discharge, the fast and medium ions of the second discharge and the fast ions of the third discharge approach the gate 3. By appropriate switching of the corona the open-gate period can be relatively short, typically around 200 μs, to produce an acceptable resolution in the spectra, whilst still ensuring that the complete range of fast, medium and slow moving ions are admitted. It will be appreciated that the apparatus could be arranged such that ions from only two successive discharges were admitted during each gate-open period. Alternatively, the apparatus could be arranged so that ions from four or more discharges were admitted.

What is claimed is:

1. An apparatus for analyzing a sample gas or vapor, the apparatus comprising:
   an ionization source disposed in an ionization chamber;
   a gate configured to control passage of ions from the ionization chamber to a drift chamber, the gate being disposed between the ionization chamber and the drift chamber; and
   a controller configured to control operation of the ionization source and the gate,
   wherein the controller is configured to control the ionization source such that the ionization source produces at least two discharges, including a first discharge and a second discharge subsequent to the first discharge, and
   wherein the controller is configured to control the gate such that:
      a start of a opening period is synchronized with the discharges such that the start of the gate opening period occurs when slower ions produced by the first discharge and faster ions produced by the second discharge approach the gate, and
      the slower ions produced by the first discharge are passed through the gate together with the faster ions produced by the second discharge during a single gate opening period.

2. The apparatus according to claim 1,
   wherein the controller is configured to control the ionization source such that the ionization source produces at least three discharges, including the first discharge, the second discharge, and a third discharge subsequent to the second discharge, and
   wherein the controller is configured to control the gate such that:
      the start of a gate opening period is synchronized with the discharges such that the start of the gate opening period occurs when the slower ions produced by the first discharge, the faster ions produced by the second discharge, and yet faster ions produced by the third discharge approach the gate, and
      the slower ions produced by the first discharge are passed through the gate together with the faster ions produced by the second discharge and the yet faster ions produced by the third discharge during a single gate opening period.

3. The apparatus according, to claim 1 wherein the apparatus comprises an ion mobility spectrometer.

4. The apparatus according to claim 1, wherein the gate comprises a first grid configured to accept a pulsed voltage.

5. The apparatus according to claim 4, wherein the apparatus further comprises a second grid, configured to accept a constant voltage to draw ions through the gate, adjacent the first grid.

6. The apparatus according to claim 1, wherein the gate's switching period is approximately 200 μs.

7. A method of analyzing a sample gas or vapor comprising:
   providing an ionization source disposed in an ionization chamber;
   providing a configured to control passage of ions from the ionization chamber to a drift chamber, the gate being disposed between the ionization chamber and the drift chamber:,
   controlling the ionization source so as to produce at least two discharges to ionize at least a portion of the gas or vapor the at least two discharges including a first discharge, and a second discharge subsequent to the first discharge;
   controlling the gate such that:
      a start of a gate opening period is synchronized with the discharges such that the start of the gate opening period occurs when slower ions produced by the first discharge and faster ions produced by the second discharge approach the gate, and
      the slower ions produced by the first discharge are passed through the gate together with the faster ions produced by the second discharge during a single gate opening period;
   applying a field to the drift chamber to cause ions in the drift chamber to move to a detector; and
   providing an output from the detector.

8. An apparatus for analyzing a sample gas or vapor, the apparatus comprising:
   a corona ionization source disposed in an ionization chamber;
   a gate configured to control passage of ions from the ionization chamber to a drift chamber, the gate being disposed between the ionization chamber and the drift chamber; and a controller configured to control operation of the corona ionization source and the gate, wherein the controller is configured to control the corona ionization source such that the ionization source produces at least two corona discharges, including a first corona discharge and a second corona discharge subsequent to the first discharge, and wherein the controller is configured to control the gate such that:

a start of a gate opening period is synchronized with the corona discharges such that the start of the gate opening period occurs when slower ions produced by the first corona discharge and faster ions produced by the second corona discharge approach the gate, and the slower ions produced the first corona discharge are passed through the gate together with the faster ions produced by the second corona discharge during a single gate opening period.

9. The apparatus according to claim 8, wherein the controller is configured to control the corona ionization source such that the corona ionization source produces at least three discharges, including the first discharge, the second discharge, and a third discharge subsequent to the second discharge, and wherein the controller is configured to control the gate such that:

the start of a gate opening period is synchronized with the corona discharges such that the start of the gate opening period occurs when the slower ions produced by the first corona discharge, the faster ions produced by the second corona discharge, and yet faster ions produced by the third corona discharge approach the gate, and the slower ions produced by the first corona discharge are passed through the gate together with the faster ions produced by the second corona discharge and the yet faster ions produced by the third corona discharge during a single gate opening period.

10. The apparatus according to claim 8, wherein the apparatus comprises an ion mobility spectrometer.

11. The apparatus according to claim 8, wherein the apparatus is configured to apply a pulsed voltage to a first grid included in the gate.

12. The apparatus according to claim 11, wherein the apparatus is further configured to apply a constant voltage to a second grid, adjacent the first grid, to draw ions through the gate.

13. The apparatus according to claim 8, wherein the gate's switching period is approximately 200 µs.

14. The apparatus according to claim 8, wherein an end of the corona ionization source is supported by an electrically insulative ferrule.

15. A method of analyzing a sample gas or vapor comprising:

providing an ionization source disposed in an ionization chamber;

providing a gate configured to control passage of ions from the ionization chamber to a drift chamber, the gate being disposed between the ionization chamber and the drift chamber;

controlling the ionization source so as to produce at least two discharges to ionize at least a portion of the gas or vapor the at least two discharges including a first discharge, and a second discharge subsequent to the first discharge;

controlling the gate such that:

a start of a gate opening period is synchronized with the discharges such that the start of the gate opening period occurs when ions having a first range of speeds produced by the first discharge and ions having a second range of speeds produced by the second discharge approach the gate, and the ions having the first range of speeds produced by the first discharge are passed through the gate together with the ions having a second range of speeds produced by the second discharge during a single gate opening period;

applying a field to the drift chamber to cause ions in the drift chamber to move to a detector; and providing an output from the detector.

16. The method of claim 15, further comprising detecting ions from the at least some ions in the first and second ranges of speeds that overlap based on the respective ions' time of flight.

17. The apparatus of claim 1, wherein the gate is configured to control an amount of the faster ions produced by the second discharge and an amount of the slower ions produced by the first discharge such that a resolution of the apparatus is not decreased with respect to a resolution achieved by a continuous ionization source.

18. The method of claim 7, wherein an amount of the faster ions produced by the second discharge and an amount of the slower ions produced by the first discharge are controlled such that a resolution of the apparatus is not decreased with respect to a resolution achieved by a continuous ionization source.

19. The apparatus of claim 1, wherein the apparatus is configured to operate at substantially atmospheric pressure.

20. The method of claim 7, wherein the method is performed at substantially atmospheric pressure.

21. The apparatus of claim 8, wherein the apparatus is configured to operate at substantially atmospheric pressure.

22. The method of claim 15, wherein the method is performed at substantially atmospheric pressure.

* * * * *